United States Patent [19]

Blay

[11] 3,965,164

[45] June 22, 1976

[54] RECOVERY OF OXIDATION CATALYST METALS FROM ADIPIC ACID PRODUCTION

[75] Inventor: Jorge A. Blay, Corpus Christi, Tex.

[73] Assignee: Celanese Corporation, New York, N.Y.

[22] Filed: Jan. 27, 1975

[21] Appl. No.: 544,159

[52] U.S. Cl............... 260/531 R; 260/537 P; 423/24; 423/63
[51] Int. Cl.²............ C07C 51/24; C07C 55/00
[58] Field of Search............ 423/23, 24, 63; 252/411, 413; 260/531 P, 537 P

[56] References Cited
UNITED STATES PATENTS

| | | | |
|---|---|---|---|
| 3,106,450 | 10/1963 | Van den Berg | 252/413 X |
| 3,148,210 | 9/1964 | Johnson et al. | 260/531 R |
| 3,186,952 | 6/1965 | Brubaker et al. | 252/413 |
| 3,564,051 | 2/1971 | Haarer et al. | 260/531 |
| 3,715,320 | 2/1973 | Jeffries | 423/24 |

FOREIGN PATENTS OR APPLICATIONS 980,762   1/1965   United Kingdom............ 423/24

Primary Examiner—Oscar R. Vertiz
Assistant Examiner—Brian E. Hearn
Attorney, Agent, or Firm—Stewart N. Rice; Ralph M. Pritchett

[57] ABSTRACT

In a process for the production of adipic acid by nitric acid oxidation of cyclohexanol and/or cyclohexanone wherein copper and vanadium values are recovered by ion exchange means, the improvement which comprises utilizing the off-gas from the nitric acid oxidation to treat the solution being passed to the ion exchange zone.

6 Claims, No Drawings

RECOVERY OF OXIDATION CATALYST METALS FROM ADIPIC ACID PRODUCTION

BACKGROUND OF THE INVENTION

In the production of adipic acid by the liquid phase nitric acid oxidation of cyclohexanol and/or cyclohexanone in the presence of a copper-vanadium catalyst there generally results a purge waste stream containing valuable copper and vanadium ions therein of which recovery is desired if the process is to operate economically. These purge waste streams are generally derived from the mother liquor of one or more crystallizations involved in the recovery of the adipic acid and the necessity for purging arises because of the buildup of other dibasic acids such as succinic acid and glutaric acid. It is obvious that in view of the value of such catalyst metals, recovery of them from the purge waste stream is desirable before discarding same.

The basic process for the nitric acid oxidation of cyclohexanol and/or cyclohexanone in the presence of a copper-vanadium catalyst is well known in the prior art. The feed mixture utilized in most industrial processes is a mixture of cyclohexanone and cyclohexanol derived from the air oxidation of cyclohexane although some processes utilize only cyclohexanol or only cyclohexanone as a feed to the nitric acid oxidation. The cyclohexanol and/or cyclohexanone is generally mixed with from 5 to 40 times its weight of an aqueous nitric acid solution, the nitric acid solution being generally of a concentration of 35 to 65% by weight, and there is also added the metal catalyst. Usually the copper and vanadium are added as ammonium metavandate and copper turnings, the total amount of catalyst usually being about 0.05 to 1.0% by weight of the reaction mixture. The liquid phase nitric acid oxidation is generally conducted at temperatures within the range of about 55° to 100°C. and pressures within the range of about 1 to 5 atmospheres absolute.

There is produced in the nitric acid oxidation a liquid reaction product comprising the adipic acid and which also contains succinic acid, glutaric acid, nitric acid, water and the copper and vanadium catalyst values. There is also produced in the nitric acid oxidation an off-gas containing nitrogen oxides such as NO, $N_2O$, $NO_2$ and $N_2O_4$ as well as other gasses such as carbon dioxide and nitrogen. Adipic acid crystals are recovered from the liquid reaction product by crystallization techniques, there resulting a mother liquor which comprises an aqueous nitric acid solution containing copper and vanadium values as well as dibasic caboxylic acids (mainly glutaric and succinic acids although some unrecovered adipic acid may also be present). A portion of this mother liquor may be and is generally recycled to the nitric acid oxidation reactor although a portion must be removed or purged to prevent buildup of the succinic and glutaric acid impurities, the portion removed or purged being the above-mentioned purge waste streams. The recovery of the adipic acid by crystallization is well known and such may be accomplished by one or more crystallization stages and may include effecting a removal of some nitric acid and water and re-dilution between crystallization steps.

Various methods have been developed for recovery of the copper and vanadium values from these purge waste streams as may be seen from U.S. Pat. Nos. 3,106,450; 3,186,952; 3,463,740; and 3,554,692. Also see British Patent Specifications 980762 and 956403.

The most popular of the methods for the recovery of the catalyst metals from the purge waste streams is by passing these streams through an ion exchange treatment zone whereby the metals are bound to the exchanger and then the metal is recovered by passing nitric acid over the exchanger. The stream resulting from the regeneration of the exchanger consists essentially of a nitric acid solution with the catalyst metals therein and, therefore, can be recycled to the nitric acid oxidation zone. While such a recovery process as well as the various known modifications thereof are fairly efficient in recovering the copper values from the purge waste streams, they do not provide as efficient recovery of the vanadium values as desired.

It is thus an object of the present invention to provide a new and useful process for the recovery of copper and vanadium values from a purge waste stream derived from the production of adipic acid by nitric acid oxidation of cyclohexanol and/or cyclohexanone. It is a particular object of the present invention to provide an improvement in the process wherein copper and vanadium values are recovered by ion exchange means from such a purge waste stream. Additional objects will become apparent from the following description of the present invention.

In the following description and in the claims, all parts and percentages are by weight unless otherwise specified.

SUMMARY

The foregoing and other objects are accomplished by the present invention which in one of its aspects is an improvement in a process for the production of adipic acid wherein (a) cyclohexanol and/or cyclohexanone are oxidized in the liquid phase by nitric acid oxidation at temperatures within the range of 55° to 100°C. utilizing a copper-vanadium catalyst to obtain a liquid reaction product comprising adipic acid and also produce a byproduct off-gas containing nitrogen oxides; and wherein (b) said reaction product is subjected to crystallization to isolate therefrom an adipic acid product and a mother liquor comprising an aqueous nitric acid solution containing therein dibasic carboxylic acids and copper and vanadium values; which improvement comprises treating at least a portion of said mother liquor to recover copper and vanadium values therefrom by: (c) concentrating said mother liquor to remove nitric acid and water therefrom and obtain a substantially dry residue containing said dibasic acids and said copper and vanadium values, the amount of nitric acid and water so removed being sufficient that the nitric acid content of said substantially dry residue is below about 5% by weight thereof and the water content of said substantially dry residue is below about 2.2% by weight thereof; (d) intimately mixing said substantially dry residue, water, and off-gas from said nitric acid oxidation to form an ultimate solution, the temperature of any aqueous solution derived from said off-gas being below 80°C. at all times, the amount of water utilized in forming said ultimate solution being at least four times the weight of said substantially dry residue and being sufficient to reduce the dibasic carboxylic acid content of the said ultimate solution to below about 17% by weight, the amount of off-gas utilized being such that the nitrous acid in the said ultimate solution derived from the off-gas, without regard to any nitrous acid present from said substantially dry residue, is at least 1% by weight of the said ultimate solution, but less than the amount of off-gas which would cause the combined total of nitric and nitrous acids in the said ultimate solution, including any nitrous and nitric acid derived from said substantially dry residue, to be greater than 3% by weight of said ultimate solution; and (e) recovering copper and vanadium values from the said ultimate solution by passing it through a bed of cation exchange resin in the hydrogen form so as to accumulate copper and vanadium ions thereon.

DETAILED DESCRIPTION OF THE INVENTION

According to the present invention, a mother liquor derived from the recovery of adipic acid by crystallization will be concentrated and mixed with the off-gas of the nitric acid oxidation reaction prior to the recovery of the copper and vanadium values by ion exchange means. The invention may be applied to all of the mother liquor from the crystallization zone although in most processes a portion of this mother liquor will be recycled. The exact makeup of a mother liquor will depend on such factors as the crystallization procedure utilized, composition of the feed to the nitric acid oxidation and the like, although a typical mother liquor will contain from about 10 to 35% nitric acid, 10 to 25% lower alkyl dicarboxylic acids (e.g. 5 to 15% glutaric, 1 to 10% succinic, and 1 to 10% adipic), 0.1 to 1.0% copper and 0.01 to 0.1% vanadium, the remainder being substantially water.

The first step in treating the mother liquor according to the invention is to concentrate such by removal of nitric acid and water from the mother liquor and form a substantially dry residue containing the catalyst metal values and which will also contain the dibasic acids present in the mother liquor. The removal of the water and nitric acid is preferably effected by using a falling film evaporator or a wiped film evaporator although distillation techniques can be utilized. Water and nitric acid form a high boiling azeotrope of about 70% nitric acid and 30% water which has a boiling point of about 122°C. at atmospheric pressure. Due to this azeotrope, when concentration of the mother liquor begins only water will initially be removed until the nitric acid/water ratio in the remaining liquid corresponds to the azeotropic composition, at which time the azeotrope will come off. The mother liquor should be concentrated to such an extent that the content of the substantially dry residue contains less than 5% nitric acid and preferably less than 3% nitric acid. Since the nitric acid and water left in the substantially dry residue will correspond to the azeotropic composition, the amount of water present will be less than about 2.2%, preferably less than 1.3%.

The next step of the process of the invention comprises intimately mixing the dry residue so obtained with water and off-gas from the nitric acid oxidation to form an ultimate solution of the three. The intimate mixing of the water, off-gas and dry residue may be accomplished in various manners and sequences it not being necessary that all three be brought into contact with each other simultaneously in one vessel. Thus the water, off-gas and residue could be simultaneously and continuously fed to a single vessel with mixing, the off-gas being bubbled through the liquid; or, the off-gas and water could be intimately contacted as by countercurrent contact in a packed column to produce a nitrogenous acidic solution which may then be intimately mixed with the dry residue. Another possible sequence is the first mixing of water with the substantially dry residue with the resulting aqueous residue solution or suspension then contacted with off-gas. When utilizing this latter sequence, which is the preferred sequence, upon mixing the water and the dry residue most of the dry residue will go into solution but some of the catalyst metal components, especially some of the vanadium compounds, may be insoluble; however, when the off-gas is introduced, these insoluble compounds will be solubilized.

Temperature is critical in the mixing of the off-gas, water and dry residue, it being important that any aqueous solution derived from the off-gas always be below 80°C., and preferably below 50°C. The temperature should be above 0°C. to prevent freezing with temperatures of 15° to 30°C. especially preferred. By the term "aqueous solution derived from off-gas" is meant an aqueous solution of the off-gas itself as well as the ultimate solution of the water, off-gas and dry residue regardless of the mixing sequence by which it was made. Thus, where off-gas is first mixed with water to form a nitrogenous acidic solution which is then mixed with the dry residue to form the ultimate solution, it is critical that the nitrogenous acidic solution resulting from mixing the water and off-gas be below 80°C., and, that the ultimate solution resulting from the mixing of the dry residue and nitrogenous acidic solution be below 80°C. In such a mixing sequence, the off-gas could be at a temperature above 80°C. (although such is not preferred) when contacted with, for example, room temperature water as long as the resulting solution were below 80°C.

Likewise when first forming an aqueous solution of the dry residue which is then intimately contacted with off-gas, the formation of the aqueous residue solution may be at any temperature desired, however, the aqueous residue solution should be at a temperature below 80°C. when contacted with the off-gas, and, the ultimate solution resulting therefrom should be below 80°C. By way of example, room temperature water may be mixed with molten dry residue having a temperature of 135°C. to form an aqueous residue solution having a temperature of about 40°C. This latter solution could then be mixed with off-gas having a temperature of 85°C. to result in the ultimate solution at about 45°C., although it is preferable that the off-gas itself be below 80°C. In most nitric acid oxidations, the oxidation reaction itself will be conducted at temperatures below 80°C. such that the offgas will be below 80°C.

The amount of water which is to be utilized in the mixing of residue, off-gas and water should be at least four times the weight of the residue and should be sufficient to reduce the dibasic carboxylic acid content of the ultimate solution below about 17% by weight thereof, preferably within the range of 10 to 17% by weight thereof. If the dicarboxylic acid content is not below about 17% by weight of the solution, unwanted crystallization of the dicarboxylic acids may occur when the solution is passed through the ion exchange resin unless undesirably high temperatures are utilized. The amount of off-gas utilized will depend on several factors, such as the amount of nitric acid in the dry residue, the amount of water utilized and the like. The ultimate solution resulting from the mixing of the off-gas, water and residue will contain nitric acid and nitrous acid most of the nitric acid being derived from that present in the residue with most of the remainder of the nitric and nitrous acids being derived from the off-gas. Enough off-gas should be utilized to contribute at least 1% by weight of nitrous acid to the ultimate solution, that is without regard to any nitric acid derived from the residue. For example, if the amount of nitrous and nitric acids in the ultimate solution would be 0.5% by weight solely because of the nitric and nitrous acids in the residue, there should be a combined total of nitrous and nitric acids in the final resulting solution of at least 1.5% because of the additional nitric and nitrous acids resulting from the off-gas. The combined total of nitric and nitrous acids in the ultimate solution should not be greater than 3% by weight because of the adverse effect such would have on the ion exchange resin capacity. Since nitric acid is a regenerator for a cation exchange resin, it should be present in as small amount as possible (2% or less, and preferably less than 1.5%) in the resulting solution to be passed through the ion exchange bed. Otherwise, the nitric acid will be attempting to regenerate the ion exchange bed and free the catalyst metal ions at the same time one is trying to retain these metal ions on the bed.

The final step of the process of the invention is to pass the solution resulting from the mixing of off-gas, water and residue through an ion exchange zone for removal of the copper and vanadium ions. The nature of the ion exchange resin employed in this invention is not particularly critical, although certain types of resin are generally preferred over others. Any of the hydrogen-form cation exchange resins disclosed in the prior art for recovering metals such as copper and vanadium can be employed. Any resin which can be employed in alternating cycles of metal absorption followed by mineral acid elution as taught in the prior art can also be employed in the present process. For example, U.S. Pat. No. 3,186,952 characterizes the applicable resins broadly as "water-insoluble polymerizate" cation exchange resins, and this term characterizes broadly the resins which are also applicable in the present process. More particularly the resins employed are those having a base comprising sulfonated polyvinyl aryl compounds which are cross-linked with a divinyl aryl compound. Specifically preferred resins include those which comprise sulfonated polystyrene cross-linked with divinylbenzene in an amount of about 8 to 25% by weight based on the weight of the resin. Commercially available resins include "Amberlite IR-200" manufactured by Rohm and Haas Company and "Dowex 50WX8", "Dowex 50X16", and "Dow SA1101.1", all manufactured by Dow Chemical Company. Many other similar resins are manufactured and can be utilized in the present process, but the resins just named are typical and illustrate the recommended materials. "Amberlite IR-200" has been found to be particularly suitable.

The geometry of the resin bed, and the space velocity to be employed in passing the aqueous feed solution through it, are not critical, nor is the particle size of the resin.

The bed is, of course, activated to its hydrogen form by treatment with a strong acid prior to passing the aqueous feed solution through it. When the ion exchange resin is exhausted as indicated by breakthrough of the metals, it may be regenerated by known methods particularly by passing aqueous nitric acid solution therethrough. The eluate will then be a nitric acid solution of the metal ions and will be a suitable source of catalyst for a nitric acid oxidation process.

When the solution containing the copper and vanadium ions derived according to the present invention is passed through the ion exchange resin, an increased amount of catalyst ions will be retained. An increased amount of vanadium in particular will be retained. It is theorized that the treatment with off-gas causes reduction of vanadic ions (having an oxidation state of plus five) to vanadous ions (having an oxidation state of plus four), the latter having more affinity for the ion exchange resin.

EXAMPLE I

A mixture of cyclohexanone and cyclohexanol was subjected to nitric acid oxidation at about 75°C. using a copper-vanadium catalyst so as to produce a liquid reaction product comprising principally an aqueous nitric acid solution of adipic acid but also containing glutaric and succinic acids. There was also produced an off-gas containing about 0.8% water, 16.2% nitrogen, 50% $N_2O$, 25% $NO_2$ and 8% $CO_2$. The liquid reaction product was concentrated in known manner by evaporation and then adipic acid recovered therefrom in known manner by crystallization leaving a mother liquor comprising mainly an aqueous nitric acid solution of adipic, succinic and glutaric acids and also containing copper and vanadium catalyst values. A portion of the mother liquor was recycled and the remainder concentrated in a wiped film evaporator to remove nitric acid and water and obtain a substantially dry residue comprising the dibasic carboxylic acids and the catalyst metal values, the nitric acid content of the substantially dry residue having been reduced to about 2.7% and the water content to about 1.2%. About 110 grams of the substantially dry residue at a temperature of 135°C. was then added to about 540 milliliters of water to reduce the dibasic carboxylic acid content of the resulting suspension to about 16.8% by weight and the nitric acid content to about 0.5%; and the suspension then cooled to about 20°C. All of the dibasic acids were in solution but some of the catalyst values were insoluble. A flask was filled about one-fourth full of the suspension and the remaining three-fourths volume of the flask filled with off-gas (which had been cooled to room temperature) from the nitric acid oxidation and the flask closed. The pressure within the flask was slightly greater than atmospheric pressure. The flask was then stirred for about 25 minutes such that nitrogen oxides in the off-gas were dissolved in the liquid residue solution to form nitric and nitrous acids and causing the insoluble catalyst values to dissolve. The nitrous acid content of the ultimate solution was about 1.5% and the nitric acid content about 1.3%. The ultimate solution contained 6100 parts per million (p.p.m.) copper and 870 p.p.m. vanadium.

The solution was then fed through a cationic type ion exchange resin in the hydrogen form located in a column 47.5 centimeters high and 2.18 centimeters in diameter. The ion exchange resin was Amberlite IR-200 ion exchange resin which is manufactured by Rohm and Haas Company and has a base comprised of a sulfonated styrene-divinylbenzene copolymer. Total resin volume was 177 cubic centimeters. Feed rate of solution through the resin was 15 milliliters per minute. The eluate was collected in 30 milliliter fractions and analyzed for copper and vanadium, and then the affinity of these metals for the resin calculated. Theoretical resin capacity was calculated to be 1.75 milliequivalents per milliliter (meq/ml) of wet resin, with the capacity for copper calculated to be 1.70 meq/ml of wet resin and the capacity for copper and vanadium combined calculated to be 1.40 meq/ml wet resin.

EXAMPLE II

The procedure of Example I was repeated except that no off-gas was utilized. Also nitric acid was added to reach the same mineral acid level as the solution of Example I which was passed through the ion exchange resin. It was found that about half of the vanadium values remained insoluble. After removing such insoluble material by filtration, the clear solution was passed through the ion exchange resin. The clear solution contained about 6100 p.p.m. copper, 490 p.p.m. vanadium, 2.6% nitric acid and 17% dicarboxylic acids. The resin capacity for copper was calculated to be 1.70 meq/ml of wet resin, and for copper and vanadium combined was calculated to be only 0.3 meq/ml of wet resin.

The embodiments of the invention in which an exclusive property or privilege is claimed are defined as follows:

1. In a process for the production of adipic acid wherein
   a. cyclohexanol and/or cyclohexanone are oxidized in the liquid phase by nitric acid oxidation at temperatures within the range of 55 to 100°C. utilizing a copper-vanadium catalyst to obtain a liquid reaction product comprising adipic acid and also produce a byproduct off-gas containing nitrogen oxides; and wherein
   b. said reaction product is subjected to crystallization to isolate therefrom an adipic acid product and a mother liquor comprising an aqueous nitric acid solution containing therein dibasic carboxylic acids and copper and vanadium values;
   the improvement which comprises treating at least a portion of said mother liquor to recover copper and vanadium values therefrom by:
   c. concentrating said mother liquor to remove nitric acid and water therefrom and obtain a substantially dry residue containing said dibasic acids and said copper and vanadium values, the amount of nitric acid and water so removed being sufficient that the nitric acid content of said substantially dry residue is below about 5% by weight thereof and the water content of said substantially dry residue is below about 2.2% by weight thereof;
   d. intimately mixing said substantially dry residue, water, and off-gas from said nitric acid oxidation to form an ultimate solution, the temperature of any aqueous solution derived from said off-gas being below 80°C. at all times, the amount of water utilized in forming said ultimate solution being at least four times the weight of said substantially dry residue and being sufficient to reduce the dibasic carboxylic acid content of the said ultimate solution to below about 17% by weight, the amount of off-gas utilized being such that the nitrous acid in the said ultimate solution derived from the off-gas, without regard to any nitrous acid present from said substantially dry residue, is at least 1% by weight of the said ultimate solution, but less than the amount of off-gas which would cause the combined total of nitric and nitrous acids in the said ultimate solution, including any nitrous and nitric acid derived from said substantially dry residue, to be greater than 3% by weight of said ultimate solution; and
   e. recovering copper and vanadium values from the said ultimate solution by passing it through a bed of cation exchange resin in the hydrogen form so as to accumulate copper and vanadium ions thereon.

2. The process of claim 1 wherein in step (c) thereof the amount of nitric acid removed from said mother liquor is sufficient that the nitric acid content of said substantially dry residue is below 3% by weight thereof, and wherein in step (d) thereof the amount of water utilized is sufficient to reduce the dibasic carboxylic acid content of the said ultimate solution to within the range of about 10 to 17% by weight.

3. The process of claim 2 wherein the temperature of any aqueous solution derived from said off-gas is below 50°C. at all times.

4. The process of claim 3 wherein the mixing of said substantially dry residue, water and off-gas is accomplished by first mixing together said residue and water to form a aqueous residue solution or suspension which, while at a temperature of below 50°C., is then further intimately mixed with said off-gas to result in a said ultimate solution having a temperature below 50°C.

5. The process of claim 3 wherein the mixing of said substantially dry residue, water and off-gas is accomplished by first mixing said water and said off-gas to result in a nitrogenous acidic solution having a temperature below 50°C. and which is then intimately mixed with said substantially dry residue to form a said ultimate solution having a temperature below 50°C.

6. The process of claim 1 wherein the temperature of any aqueous solution derived from said off-gas is below 50°C. at all times.

* * * * *